United States Patent [19]

Hiss, III et al.

[11] Patent Number: 6,016,688
[45] Date of Patent: Jan. 25, 2000

[54] IN-STACK DIRECT PARTICULATE MASS MEASUREMENT APPARATUS AND METHOD WITH PRESSURE/FLOW COMPENSATION

[75] Inventors: John Hiss, III, Castleton; Harvey Patashnick, Voorheesville, both of N.Y.

[73] Assignee: Rupprecht & Patashnick Company, Inc., Albany, N.Y.

[21] Appl. No.: 09/190,657

[22] Filed: Nov. 12, 1998

Related U.S. Application Data

[63] Continuation-in-part of application No. 09/078,909, May 14, 1998.

[51] Int. Cl.[7] .......................... G01N 15/06; B01D 53/30; G01G 3/14; G08B 21/00
[52] U.S. Cl. .................. 73/28.01; 73/23.33; 73/863.23; 73/31.07; 422/88
[58] Field of Search ................ 73/28.01, 28.03, 73/28.04, 23.33, 863.25, 863.23, 865.5, 28.05, 31.07; 422/83, 88, 101; 436/137, 807

[56] References Cited

U.S. PATENT DOCUMENTS

| | | | |
|---|---|---|---|
| 2,982,131 | 5/1961 | Rosinski | 73/170 |
| 3,005,347 | 10/1961 | Smithson | 73/423 |
| 3,068,694 | 12/1962 | Worswick | 73/194 |
| 3,633,405 | 1/1972 | Noll | 73/28 |
| 3,707,869 | 1/1973 | Raynor | 73/28 |
| 3,784,902 | 1/1974 | Huber | 324/32 |
| 3,841,145 | 10/1974 | Boubel | 73/28 |
| 3,926,271 | 12/1975 | Patashnick | 177/210 |
| 3,965,748 | 6/1976 | Boubel et al. | 73/421.5 A |
| 4,007,754 | 2/1977 | Beck et al. | 137/2 |
| 4,114,557 | 9/1978 | De Brey | 116/67 R |
| 4,391,338 | 7/1983 | Patashnick | 177/210 |
| 4,442,699 | 4/1984 | Ramelot | 73/28 |
| 4,550,591 | 11/1985 | Cox et al. | 73/28 |
| 4,660,408 | 4/1987 | Lewis | 73/28 |
| 4,815,314 | 3/1989 | Plank | 73/28 |
| 5,006,227 | 4/1991 | Behm et al. | 209/143 |
| 5,090,233 | 2/1992 | Kogure et al. | 73/28.05 |
| 5,110,747 | 5/1992 | Pataschnick et al. | 436/133 |
| 5,369,981 | 12/1994 | Merz et al. | 73/28.01 |
| 5,571,945 | 11/1996 | Koutrakis et al. | 73/28.03 |
| 5,571,946 | 11/1996 | Koshi et al. | 73/28.01 |
| 5,665,902 | 9/1997 | Wang et al. | 73/28.01 |
| 5,739,413 | 4/1998 | Kohn et al. | 73/23.31 |

FOREIGN PATENT DOCUMENTS 2-324364  7/1992  Japan .

OTHER PUBLICATIONS

"EPA Stationary Source Sampling Methods", Rules and Regulations, Feb. 23, 1978, pp. 17–1 through 17–8.
"Operating Manual Addendum TEOM Series 1105 Diesel Particulate Mass Monitor", Rupprecht & Patashnick Co., Inc., Albany, NY, Sep. 1997, 54 pp.

*Primary Examiner*—Hezron Williams
*Assistant Examiner*—J. David Wiggins
*Attorney, Agent, or Firm*—Heslin & Rothenberg, P.C.

[57] ABSTRACT

The mass of particulate of an effluent gas flowing in a stack is directly measured with a mass measurement assembly supported within the stack. The mass measurement assembly preferably includes an inertial mass measurement transducer which provides near real-time mass readings. The mass measurement assembly also includes a particulate collector which can be equilibrated in situ. A pressure transducer measures a pressure differential across the equilibrated collector prior to sampling, to determine a pressure coefficient of frequency in a calibration operation. The pressure transducer also measures a pressure differential across the collector during sampling which measurement is used along with the pressure coefficient of frequency to derive an adjusted mass reading, corrected to compensate for pressure changes.

25 Claims, 7 Drawing Sheets

Fig. 4 Detail of Time Proportioned Step Change

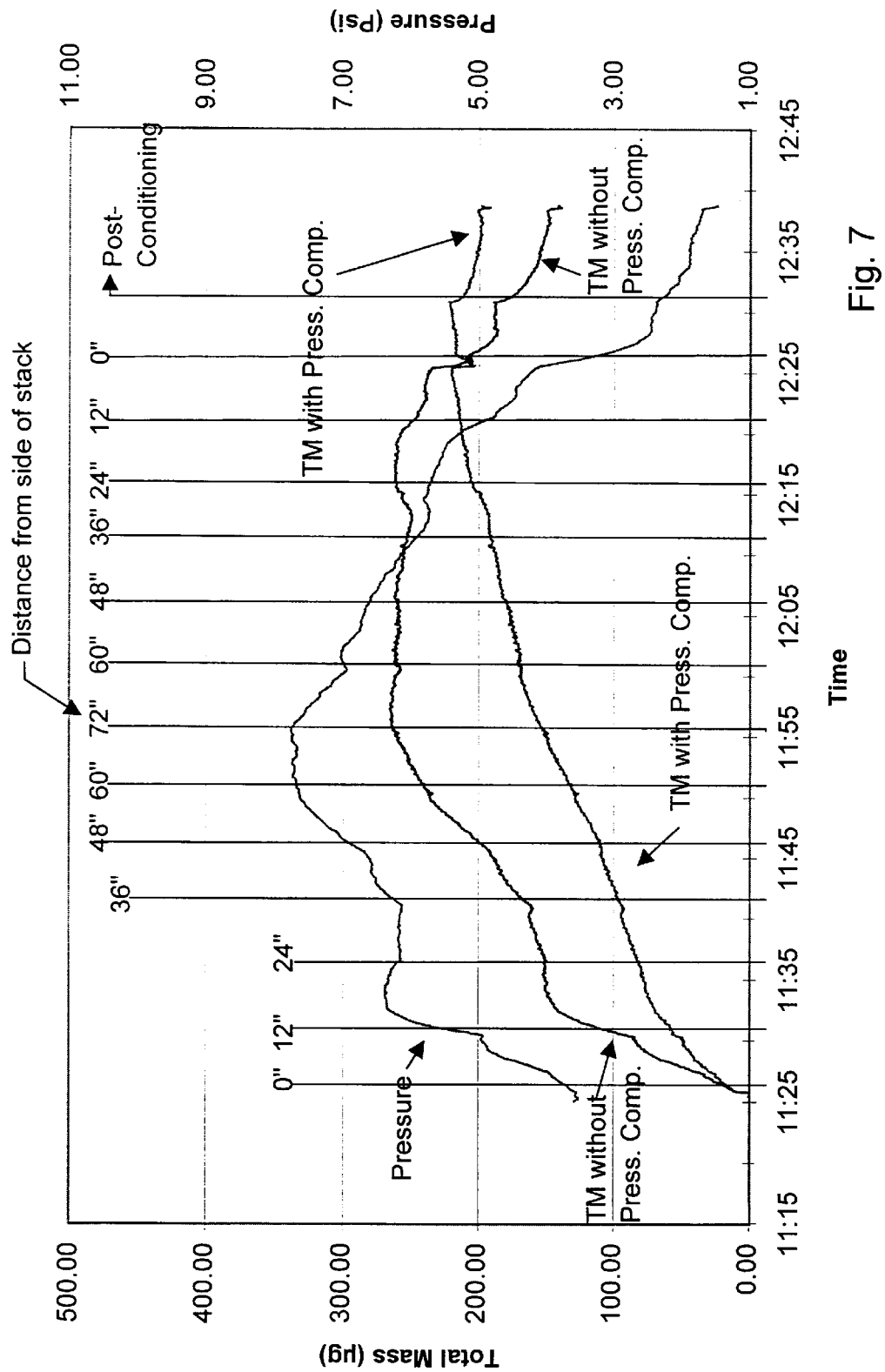

IN-STACK DIRECT PARTICULATE MASS MEASUREMENT APPARATUS AND METHOD WITH PRESSURE/FLOW COMPENSATION

RELATED APPLICATION

This application is a continuation-in-part of commonly assigned application Ser. No. 09/078,909, filed May 14, 1998, and is related to commonly assigned application Ser. No. 09/014,252, filed on Jan. 27, 1998, which applications are incorporated herein by reference in their entirety.

FIELD OF THE INVENTION

This invention relates generally to particulate matter mass measurement instruments, and more particularly to such instruments used to collect and measure particulate matter of effluent gas flowing in a stack or other exhaust conduit of a stationary source.

BACKGROUND ART

The measurement of particulate matter of effluent gas flowing in a stack or other exhaust conduit of such stationary sources as coal burning facilities, garbage incinerators, hazardous waste type incinerators, concrete plants, paper/pulp processing plants and the like, is important because of the relationship between particulate matter and adverse health effects. Particulate matter exiting a stack of such an industrial source disburses into the atmosphere where it is inhaled by humans. Suspended particulate matter is known to produce a variety of deleterious health effects when inhaled. Monitoring of the particulate mass and/or concentration of the effluent gas in a stack is, therefore, important for health reasons.

Particulate matter exiting a stack is made up of many regulated substances. Measurement of particulate matter mass can also be used as a surrogate measurement of these other regulated substances.

Accordingly, regulatory agencies around the world require the continuous measurement of particulate matter emissions from stacks. A disadvantage of all present continuous stack particulate monitors—opacity, triboelectric, acoustical, and beta attenuation—is that they do not directly weigh particulate and must be periodically calibrated using manual mass measurements.

Manual measurement methods are defined in terms of utilizing a filter medium to capture particulate matter while measuring the total volume of effluent gas which has been filtered at the stack temperature by the medium over a period of time. There are various approaches available to unambiguously determine the flow rate through the filter over time and, hence the volume of gas sampled. However, effluent gas often contains water which adds non-particulate mass to the filter medium. To accurately represent the filter mass, the uncombined water must be removed.

As a result, the current Environmental Protection Agency (EPA) reference method (Method 17) in the United States is a manual method that requires the removal of uncombined water prior to and following particulate collection. The manual method consists of: (1) filter equilibration under a predefined range of temperature and humidity conditions; (2) a pre-collection weighing of the filter; (3) the installation of the filter in the manual sampler and the obtaining of a representative effluent gas sample from within the stack; (4) the removal of the filter from the stack and the sampler, and post-collection clean up of the nozzle and housing (all particulate on the walls of the nozzle and filter housing leading to the filter medium must be collected as part of the sample); (5) post-collection conditioning under the same equilibrium conditions for the filter as performed in the preconditioning (this procedure removes uncombined water from the sample and filter medium); and finally, (6) post-collection weighing of the filter to determine the mass captured on the filter medium. Steps (1), (2), (5) and (6) are normally implemented in the controlled environment of a laboratory remote from the stack. Because of the filter and apparatus handling required, this manual measurement method contains many opportunities for measurement error. It is also very labor intensive, tedious and expensive. The method provides only an average particulate concentration for the sample period, and requires a great deal of care to give repeatable results because of the many inherent sources of error such as filter handling, transport, conditioning and weighing. Another disadvantage is that useful time history information, describing transients and stack stratification, is lost. An easier, faster, more repeatable technique would also allow for more accurate and frequent calibrations of the present indirect continuous emission monitors.

Obtaining a representative particulate sample from a particulate laden effluent gas stream generally requires that the sample be obtained isokinetically. That is, a particle traveling in the sample inlet must possess the same kinetic energy as a particle traveling in the effluent gas stream. Since kinetic energy is a function of only mass and velocity, mass being constant, isokinetic sampling requires that the particle velocity at the entrance of the sample inlet must match the particle velocity of the effluent gas. Industrial processes that produce effluent gas streams are continuously changing, resulting in continuous velocity changes over time. Also, the velocity profile across an effluent conduit or stack is not constant, resulting in required instrument flow changes during traverse sampling. Therefore, for a measurement to remain isokinetic, the instrument sample flow must be altered also. When instrument sample flow is altered to maintain isokinetics, pressure changes in the measurement device are experienced and may result in erroneous mass readings if not properly controlled or accounted for.

A need thus persists for a particulate mass measurement instrument which reduces many of the error sources associated with manual and isokinetic sampling, and provides more representative data, easier, faster and with enhanced accuracy.

SUMMARY OF THE INVENTION

This need is satisfied, shortcomings of the existing art are overcome, and additional benefits are realized, in accordance with the principles of the present invention, through the provision of an in-stack mass measurement instrument which accurately measures mass of particulate of effluent gas directly and in near real-time. Further, in-stack equilibration of the particulate collector eliminates the need for pre- and post-sampling laboratory work, and pressure/flow calibration and compensation reduces mass measurement errors resulting from pressure/flow changes.

In accordance with a first aspect of the present invention, apparatus for directly measuring mass of particulate of effluent gas flowing in a stack includes an inertial mass measurement assembly. This assembly includes a mass transducer, a particulate collector connected to the mass transducer, and an inlet tube for directing sampled gas towards the collector. A support structure supports the mass measurement assembly within the stack with the inlet tube oriented for sampling effluent gas flowing in the stack. Accordingly, sampled effluent gas enters the tube and is directed toward the collector. A pressure transducer measures a pressure differential across said collector and a processor or controller determines an adjusted mass reading based upon said measured pressure differential.

The pressure transducer measures a differential between a first pressure upstream of the collector and a second pressure downstream of the collector. A first pressure tap line senses the first pressure and a second pressure tap line senses the second pressure. The first and second pressure tap lines are connected to the pressure transducer. Alternatively, the first pressure may comprise a pressure of the effluent gas flowing in the stack, or ambient air pressure.

The mass measurement apparatus can further include a sampling line for conveying sampled gas from the collector to a control unit outside the stack. The control unit includes a flow controller for varying flow of the sampled gas in the sampling line to maintain isokinetic sampling of the effluent gas at an entrance to the inlet tube. The pressure transducer can measure a pressure differential across the collector related to the varying flow of sampled gas.

In a preferred embodiment, the mass transducer comprises a hollow elastic element mounted to vibrate in a clamp-free mode, and the collector comprises a filter mounted on a free end of said elastic element. The sampled gas is drawn through the filter and the hollow elastic element.

The particulate mass measurement apparatus of the present invention preferably also includes an in-situ equilibrator for equilibrating the collector within the stack. The in-situ equilibrator may comprise a supply line for selectively supplying conditioned gas to the collector while the mass measurement assembly is supported within the stack. The conditioned gas advantageously prevents effluent gas from reaching the collector. A controller mandates supply of the conditioned gas to the collector prior to a sampling period to precondition the collector.

Calibration means are advantageously employed to determine pressure coefficient of frequency of the collector following preconditioning. The calibration means includes the differential pressure transducer. The processor employs the pressure coefficient of frequency in determining the adjusted mass reading.

The pressure coefficient of frequency is preferably determined in accordance with the following formula:

$$PC = (f_2 - f_1)/((f_2 + f_1)/2)/(P_2 - P_1)$$

where:

PC represents the pressure coefficient of frequency;

$f_1$ and $P_1$ represent a frequency of oscillation of the mass transducer, and a pressure differential measured by said pressure transducer, respectively, at a time $T_1$; and $f_2$ and $P_2$ represent a frequency of oscillation of the mass transducer, and a pressure differential measured by said pressure transducer, respectively, at a time $T_2$.

The time $T_1$ is normally associated with a first sampled gas flow rate from the collector, and the time $T_2$ is associated with a second different sampled gas flow rate from the collector. A similar approach employing sensed fluid flow rates and a flow coefficient of frequency is also contemplated.

In another aspect of the present invention, a mass measurement device wherein material from a sampled gas is collected on a collector for mass measurement purposes, is improved through the provision of: a pressure transducer for measuring a pressure differential across the collector, and a processor for determining an adjusted mass reading based upon the measured pressure differential.

A method for measuring mass of material in an effluent gas flowing in a stack is also provided by the present invention. The method includes: locating a material collector within the stack; calibrating the collector to generate a pressure coefficient of frequency; collecting material from sampled effluent gas on the collector within the stack during a sampling period; and measuring a mass change of said collector for the sampling period. This method may further include the steps of measuring change in pressure across the collector for the sampling period, and employing said pressure coefficient of frequency and measured change in pressure to derive an adjusted mass reading for the sampling period. The adjusted mass reading accounts for effects attributable to the change in pressure across the collector.

The present invention also provides an improvement to a method of generating a reading of mass of particulate collected from a gas stream by a collector mounted to a mass transducer of an inertial mass measurement instrument. This improvement comprises compensating said reading in response to a measured change in pressure across the collector. More particularly, a pressure coefficient of frequency for the mounted collector is determined, a change in pressure across the collector for a sampling period is measured, and the pressure coefficient of frequency and measured change in pressure are employed to derive an adjusted mass reading for the sampling period. This adjusted mass reading accounts for effects attributable to the change in pressure across the collector.

The mass measurement instrument and methodology of the present invention directly measures particulate mass concentrations of effluent gas in a stack in near real-time. This instrument may be used to perform EPA Method 17 equivalent test, as well as short-term continuous sampling. In addition, because it resolves mass on line in near real-time, the apparatus of the present invention provides useful plant process information such as transient particulate mass concentrations during ramped loadings, stratification in stacks and control device efficiencies. Another valuable use for the instrument of the present invention is to calibrate existing continuous emission monitors such as opacity, triboelectric, acoustical and beta attenuation monitors that, unlike the present invention, do not possess a direct relationship with particulate mass. The present invention further eliminates the need to transport the sample to a lab for conditioning and weighing, and compensates for pressure/flow changes. The operation of the instrument of the present invention thus reduces testing errors and provides an accurate and repeatable test protocol.

Many of these advantages can also be realized in applications other than stack monitors, by, for example, including the pressure/flow compensator of the present invention in other mass measuring instruments where it is desirable to compensate for pressure changes across a collector associated with variations in sampling flow rates or other causes.

BRIEF DESCRIPTION OF DRAWINGS

These and other aspects, features and advantages of the invention will become more readily apparent upon reference to the following detailed description of preferred embodiments when read in conjunction with the accompanying drawings, in which:

FIG. 7 is a graphical representation illustrating how the pressure/flow compensator removes errors from measured mass readings.

DETAILED DESCRIPTION

Figure 1:
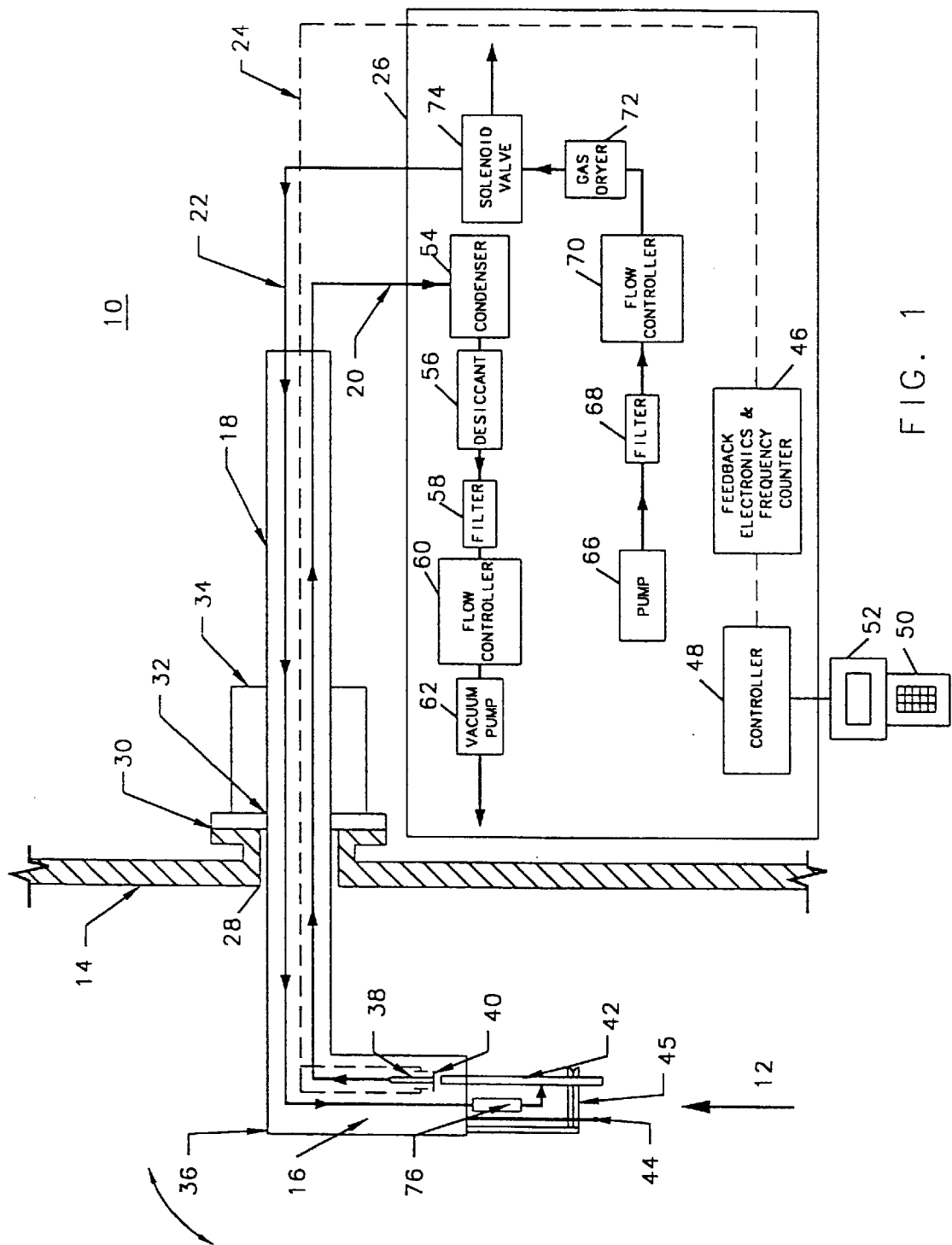
FIG. 1 is a schematic representation of an embodiment of the particulate mass measurement apparatus of parent application Ser. No. 09/078,909 as it can be employed to determine the mass of particulate of effluent gas flowing within a stack.

A particulate mass measurement instrument 10 for measuring the mass of particulate in an effluent gas 12 flowing within a stack 14 in accordance with the principles of parent application Ser. No. 09/078,909, is illustrated in FIG. 1. This instrument directly measures particulate mass on-line in near real-time with provision for in-stack conditioning of the particulate collector, as more fully described hereinafter.

Mass measurement instrument 10 includes a mass measurement assembly or probe 16 supported within stack 14 at the end of an extendible boom 18, or other support structure. The mass measurement assembly 16 is connected via pneumatic lines 20, 22 and electrical signal line 24 to a control unit 26. The pneumatic and electrical signal lines preferably extend along and through boom 18. Advantageously, pneumatic lines 20 and 22 can be controllably heated, in whole or part, as more fully described hereinafter. Control unit 26 may be located proximate boom 18 or remote therefrom.

Mass measurement instrument 10 is intended for use in measuring the mass of particulate in an effluent gas 12 flowing in a stack 14. The term "stack" is broadly used herein to connote any passageway that has particulate laden gas flowing through it. The term "effluent gas" is used herein to denote any such particulate laden gas. The invention is applicable to any facility which emits particulate laden gas. Such facilities are sometimes referred to in this industry as "stationary sources" and include, but are not limited to: coal burning facilities, garbage incinerators, hazardous waste type incinerators, cement plants, paper/pulp processing facilities, boiler exhaust, and smoke stacks.

As shown in FIG. 1, the wall of stack 14 might typically include a port 28 defined by an exterior flange 30. According to one embodiment of the present invention, a sliding joint 32 and bearing housing 34 are mounted to an outside surface of flange 30. Port 28, sliding joint 32 and bearing housing 34 define an interior passageway through which measurement assembly 16 and boom 18 can be inserted into stack 14. Assembly 16 and boom 18 have an outer diameter slightly smaller than that of port 28. Assembly 16 is mounted to the end of boom 18 by a rotating joint or pivot 36. This joint allows assembly 16 to be-oriented coaxially with boom 18 for access into stack 14 through port 28. Following insertion, mass measurement assembly 16 is rotated about joint 36 to an orientation, as shown in FIG. 1, which facilitates sampling of effluent gas 12. After sampling is completed, assembly 16 can be rotated back to its coaxial orientation with boom 18 for ready withdrawal from stack 14 through port 28. Various conventional mechanisms can be used to provide the rotational support and movement to assembly 16, as will be appreciated by those skilled in this art.

While port 28 provides access to the interior of stack 14, sliding joint 32 and bearing housing 34 allow the boom 18 and attached mass measurement assembly 16 to be displaced in order to traverse the interior of the stack, as may be required or desired under various measurement protocols. A quick release clamp (not shown) may be used to temporarily lock slidable boom 18 in place when measurement assembly 16 is positioned at a desired crosswise location within stack 14. Boom 18 is preferably extendible to a maximum desired traverse length, and collapsible to adapt to various field conditions and for ease of transport.

Mass measurement assembly 16 includes a mass transducer 38 connected to a mass collector 40, and an inlet tube 42 for directing sampled effluent gas 12 towards particulate collector 40. Although the components of mass measurement assembly 16 may take many different forms, mass transducer 38 is preferably an inertial mass measurement transducer which provides a direct, near real-time measure of the mass of particulate collected on collector 40. Transducer 38 can advantageously take the form of a hollow elastic element oscillating in a clamp-free mode, as more fully described hereinafter. Collector 40 preferably comprises a filter mounted to transducer 38. An impaction plate or other particulate matter collector can also be used to collect particulate from the sampled effluent gas. Inlet tube 42 is preferably short and straight to minimize inlet losses.

Mass measurement assembly 16 can be used to measure total particulate mass levels, or in conjunction with a cyclone or other device (not shown) that separates particles based on aerodynamic diameter, located upstream of inlet tube 42, to measure $PM_{10}$ or $PM_{2.5}$ particulate mass levels as is well known in the art. Similarly, assembly 16 can be outfitted with a temperature sensor 44 and a pressure sensor 45, e.g. pitot tubes, to facilitate and maintain isokinetic sampling at the entrance of inlet tube 42 as is well known in the art and specifically taught by EPA Method 17—Determination of Particulate Emissions From Stationary Sources (In-Stack Filtration Method), pages 17-1 to 17-8, Rev. 1, dated August 1985 (which document is incorporated by reference herein in its entirety). Although presently preferred, isokinetic sampling may not be necessary when measuring small particulate.

Particulate collector 40 is preferably located near the exit of inlet tube 42 in order to minimize transport losses and ensure integrity of the sample. Collector 40 preferably comprises an exchangeable filter cartridge mounted on the free end of the preferred transducer—a hollow elastic element which is made to oscillate in a clamp-free mode. Construction and operation of an inertial mass measurement instrument employing such an oscillating hollow elastic element is described in detail in commonly assigned U.S. Pat. Nos. 3,926,271 and 4,391,338, and in a Japanese patent publication JP2-324364 (which patents and Japanese patent publication are incorporated herein in their entirety) and is briefly described hereinafter.

The mass transducer 38 is preferably a hollow tube, clamped at one end and free to vibrate at the other. An exchangeable filter cartridge is placed over the tip of the free end. This cantilevered elastic element vibrates at precisely its natural frequency. An electronic control circuit 46 senses its vibration and, through positive feedback, adds sufficient energy to the system to overcome losses. An automatic control circuit (not shown) maintains the vibration during measurement. A precise electronic counter 46 measures the frequency, which has a direct relationship with mass.

The elastic element is a mechanical oscillator with a high quality factor whose frequency can be described with two parameters, the restoring force constant, K, and the mass, m, consisting of the mass of the filter, $m_f$, the effective mass of the elastic element, $m_0$, and the filter loading $\Delta m$.

$$m = m_f + m_0 + \Delta m \tag{1}$$

The relationship between these quantities is given by the simple harmonic oscillator equation:

$$4\pi^2 f^2 = K/m \tag{2}$$

or $$f^2 = K_0/m \text{ with } K_0 = K/4\pi^2 \tag{3}$$

Calibration Process

If a known mass, $\Delta m$ (determined gravimetrically) is placed on the filter, $K_0$ can be determined from the frequencies $f_1$ and $f_2$ where $f_1$ is the frequency without $\Delta m$, and $f_2$ is the frequency after loading with $\Delta m$.

$$f_1^2 = K_0/(m_f + m_0) \tag{4}$$

$$f_2^2 = K_0/(m_f + m_0 + \Delta m) \tag{5}$$

From these two equations $K_0$ can be calculated for a particular device:

$$K_0 = \Delta m/(1/f_2^2 - 1/f_1^2) \tag{6}$$

The elastic element is made of nonfatiguing inert material and retains its calibration indefinitely.

Mass Measurements

Once $K_0$ is determined for a particular elastic element, it can be used for mass measurements.

If the element is oscillating at the frequency of $f_a$ and exhibits the frequency $f_b$ after an unknown mass uptake $\Delta m'$, this mass uptake can be obtained as a function of $f_a$, $f_b$ and $K_0$. It is:

$$f_a^2 = K_0/m \tag{7}$$

$$f_b^2 = K_0/(m + \Delta m') \tag{8}$$

where m is the total mass of the system before the mass uptake. Elimination of m yields the fundamental equation for mass uptake.

$$\Delta m' = K_0(1/f_b^2 - 1/f_a^2) \tag{9}$$

This calculation can be further refined to compensate for pressure/flow changes across the collector associated with isokinetic sampling, as described hereinafter. Note that the starting frequency, $f_a$, can be defined at any arbitrary time, and a mass measurement does not depend on the knowledge of the previous loading of the filter. Tracking frequency with time yields the mass rate, and when combined with measured flow rate through the filter, produces the mass concentration. Such tracking and calculations can be readily accomplished, in known fashion by a computer/controller or processor 48 in control unit 26. A keypad 50 and display 52, or other input/output devices can be connected to controller 48 to facilitate operator interface therewith and to indicate mass readings provided by instrument 10.

Referring again to FIG. 1, sampling line 20 connects mass transducer 38, e.g. the described hollow elastic element, to a condenser 54 located outside of stack 14. At least a portion of sampling line 20 is preferably heated to prevent moisture condensation therein. Condenser 54 in conjunction with optional desiccant 56 serve to remove moisture and thoroughly dry the sampled gas before it passes through an additional optional filter 58, mass flow controller 60 and is exhausted through reduced pressure (e.g. vacuum) pump 62.

In operation, effluent gas 12 enters inlet tube 42 and passes directly therethrough to collector 40 mounted on the oscillating element or other mass transducer 38. The particulate matter in the sampled effluent gas can be collected by collector 40 at stack temperature as described in EPA Method 17. The sampled gas then proceeds through heated sampling line 20 in boom 18 to condenser 54 and then through the remaining elements of the sampling train. In this manner, direct measurements of the mass of particulate matter deposited on collector 40 can be obtained in near real-time on-site.

EPA Method 17 requires the removal of uncombined water from a collected sample. Mass measurement instrument 10 provides for in-stack purging of such uncombined water, as well as equilibration of the collector prior to and after sampling. Equilibration comprises establishing a stable, reproducible thermodynamic condition for the collector before and/or after sampling. Collector conditioning between intermittent sampling periods can also be effectuated.

In accordance with this feature of the instrument, a conditioned gas line 22 extends through boom 18 and connects to inlet tube 42 in order to selectively supply conditioned gas to collector 40. The conditioned gas preferably comprises a dry clean gas provided by pump 66 through a filter 68, flow controller 70, gas dryer 72, and solenoid valve 74 to line 22. The components of this conditioned gas train may be conventional, off-the-shelf type elements. Such elements are preferably located in control unit 26 outside of stack 14.

Also associated with conditioned gas line 22 is a heat exchanger 76 or other conditioned gas temperature controller. As shown in FIG. 1, heat exchanger 76 is preferably located within stack 14 to conveniently ensure that the conditioned gas stream is at the effluent gas temperature. The heat exchanger may be either active, passive or a combination of both active and passive. Temperature sensor 44 can be employed for such active control. The heat exchanger may take various known forms. A section of conditioned gas line 22 upstream of heat exchanger 76 can optionally be heated to preheat said gas entering the exchanger.

If desired, heat exchanger 76 or other temperature controller can be used to adjust the temperature of the conditioned gas to any set temperature, e.g. a temperature higher than that of the effluent gas.

Flow controller 70 controls the rate of flow of the conditioned gas while filter 68 and gas dryer 72 serve to ensure that the conditioned gas is clean and dry. Solenoid valve 74 serves to quickly turn on and off the supply of conditioned gas to line 22. When not in use, the conditioned gas is exhausted through solenoid valve 74. The activation and operation of the components of the conditioning gas train, as well as the components of the sampling train can all be controlled by controller 48, in known fashion.

The conditioned gas can advantageously be provided with a flow rate greater than that of the sampled effluent gas so that when collector 40 is to be conditioned, equilibrated, pressure/flow calibrated and/or purged by the conditioned gas, effluent gas is prevented from reaching the collector, i.e. backflow of the conditioned gas towards the entrance of inlet tube 42 due to its higher flow rate effectively blocks the entry of effluent gas into tube 42.

Alternatively, the flow along sampling line 20 can be controlled to effectively dilute the sampled effluent gas with conditioned gas. This approach might be used to extend collector life or to reduce the amount of moisture reaching the collector in order to enhance the ability of the collector to collect particulate or to decrease any postconditioning time.

When the flow rate of the conditioned gas is such as to prevent effluent gas sampling, the conditioned gas can be employed to equilibrate collector 40 in situ. Such equilibration can be used to precondition the collector prior to sampling and to postcondition the collector and any collected particulate after sampling, yielding results directly comparable to EPA Method 17, while avoiding the difficulties and delays associated with laboratory equilibration. Such collector conditioning can also be effectuated between intermittent sampling periods thereby extending the available life of the collector.

The conditioned gas line can provide for a constant stable flow rate to and a constant temperature at the collector during conditioning and sampling. In situ conditioning thus does not disturb the state of the collector-mass transducer combination.

The in-stack particulate mass measurement instrument of FIG. 1 may be operated in various modes: continuous measurements at a single point, timed traverse measurements at multiple points, or time proportioned (intermittent) sampling, e.g. for calibration of indirect continuous emission monitors. Continuous uninterrupted sampling is used for relatively short duration tests, on the order of a few hours, similar to an EPA Method 17. Because collector life is a function of the type of particulate matter as well as the concentration, test durations on the order of days may be possible.

Collector life can be extended by sampling for only a portion of the time. This "time proportioned sampling" technique lengthens the time between collector changes, and can be used to calibrate present continuous monitors on a regular basis. For example, a scheme where sampling by instrument 10 occurs for a short time each hour and is compared with opacity readings taken by a separate continuous emission monitor during the same period would allow the constant updating of the continuous monitor calibration.

Figure 2:
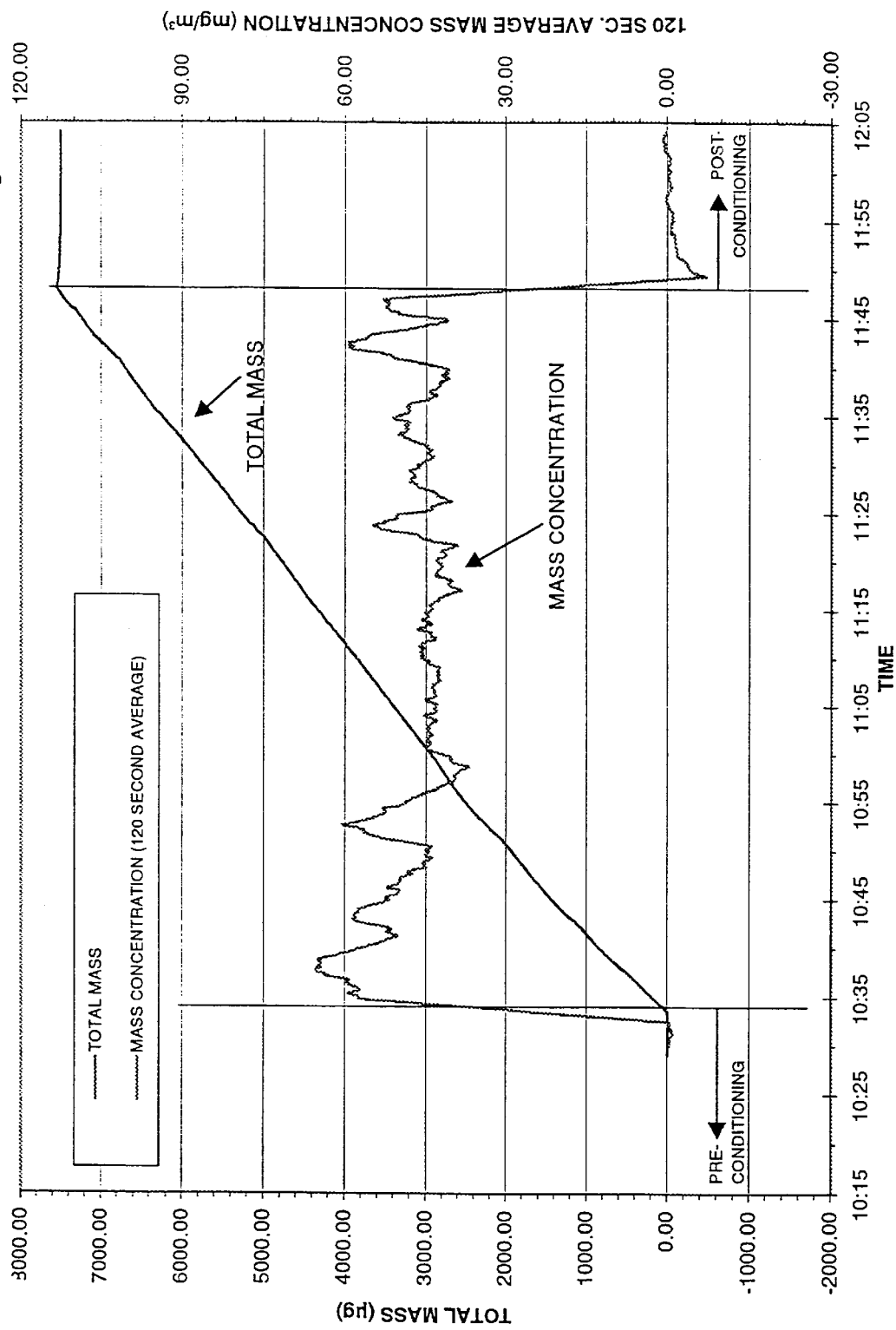
FIG. 2 is a graphical representation of total mass and mass concentration readings from an in-stack particulate mass measurement instrument of FIG. 1 during in-situ preconditioning, continuous sampling, and in-situ postconditioning time periods.

A typical sequence of operation for the particulate mass measurement instrument 10 will now be described. Initially the complete instrument is checked for leaks and then a collector 40 is installed in mass measurement assembly 16. Assembly 16 coaxially aligned at the end of boom 18 is then inserted through access port 28 into stack 14 and rotated into its sampling position with conditioned gas line 22 activated. The flow rate of the conditioned gas into inlet tube 42 prevents any effluent gas 12 from reaching collector 40 and permits preconditioning of this collector within the stack. The instrument is allowed to stabilize, i.e. the temperature of the conditioned gas, due to the heat exchanger or other temperature controller, rises to that of the effluent gas. As shown in FIG. 2 this preconditioning establishes a zero baseline for future mass readings.

Once the collector has been preconditioned, sampling can begin by activating solenoid valve 74 to shut off the supply of conditioned gas to collector 40. Sampling line 20 now draws effluent gas in through inlet tube 42 for collection of particulate matter on collector 40. As illustrated in FIG. 2 during sampling, the total mass and/or mass concentration of the effluent gas can be directly determined and indicated in known fashion by the particulate mass measurement instrument.

At the conclusion of sampling, solenoid valve 74 is again activated to supply the conditioned gas to inlet tube 42. The higher flow rate of the conditioned gas again blocks effluent gas from reaching the collector. The dry, clean, heated conditioned gas removes uncombined water and serves to postcondition the collector and collected particulate, as illustrated in FIG. 2.

Figure 3:
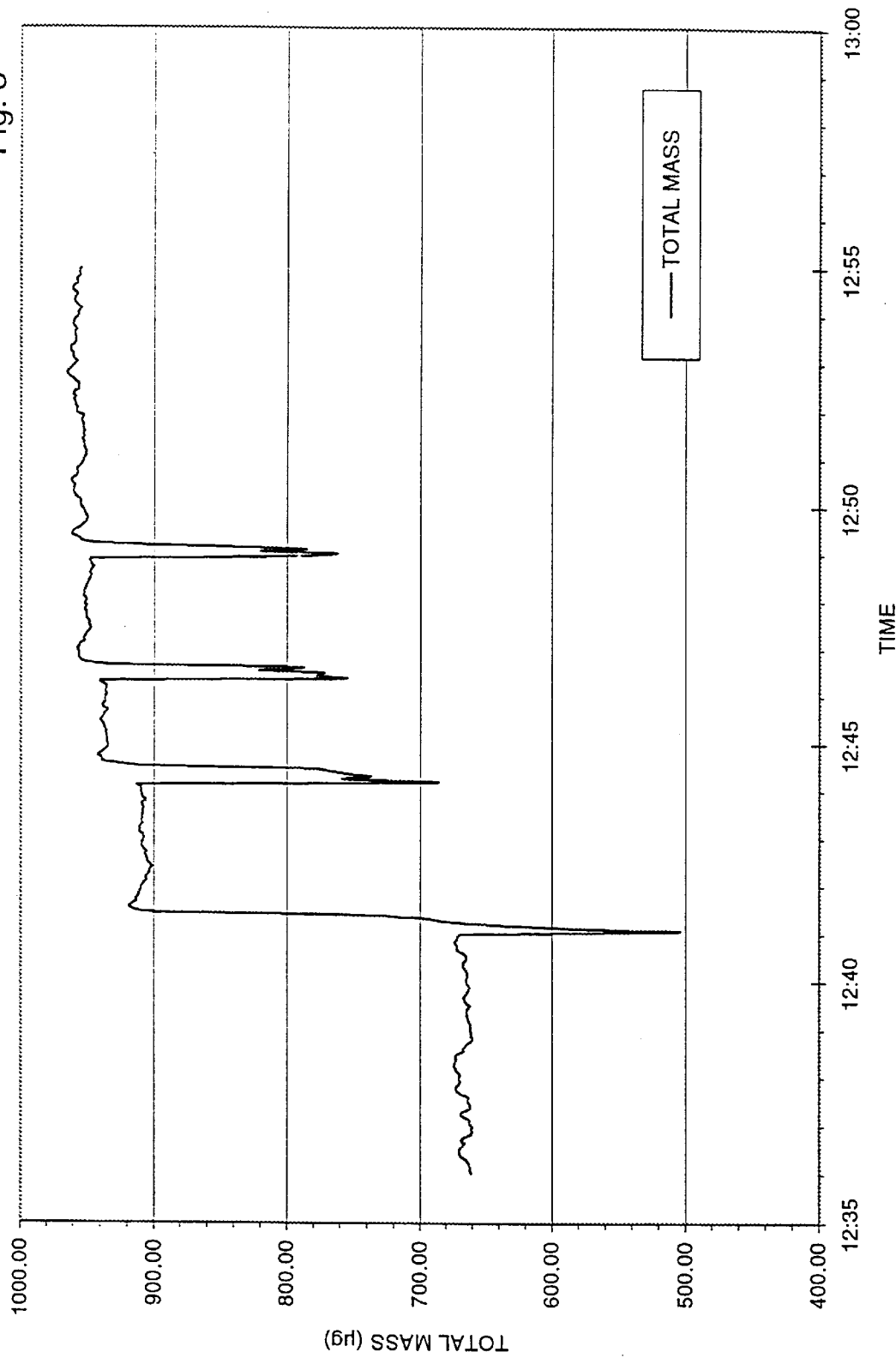
FIG. 3 is a graphical representation of total mass readings provided by an instrument like that illustrated in FIG. 1 during several brush downs of the interior of an inlet tube of the instrument.

Following the postconditioning, assembly 16 is withdrawn from stack 14 through access hole 28, the conditioned gas line 22 is deactivated and assembly 16 is preferably temperature stabilized outside the stack, for example with an insulation blanket, to maintain assembly 16 at substantially the stack temperature. With the sampling line 20 still activated, the interior of inlet tube 42 can then be brushed down several times to collect and measure, using the same measurement instrument 10, any particulate matter which may have lodged along the interior walls of the tube during sampling. Mass readings resulting from brush down are illustrated in FIG. 3. The mass reading from brush down can be added to the mass reading obtained during sampling to provide a more accurate indication of the total mass particulate in the effluent gas.

Figure 4:
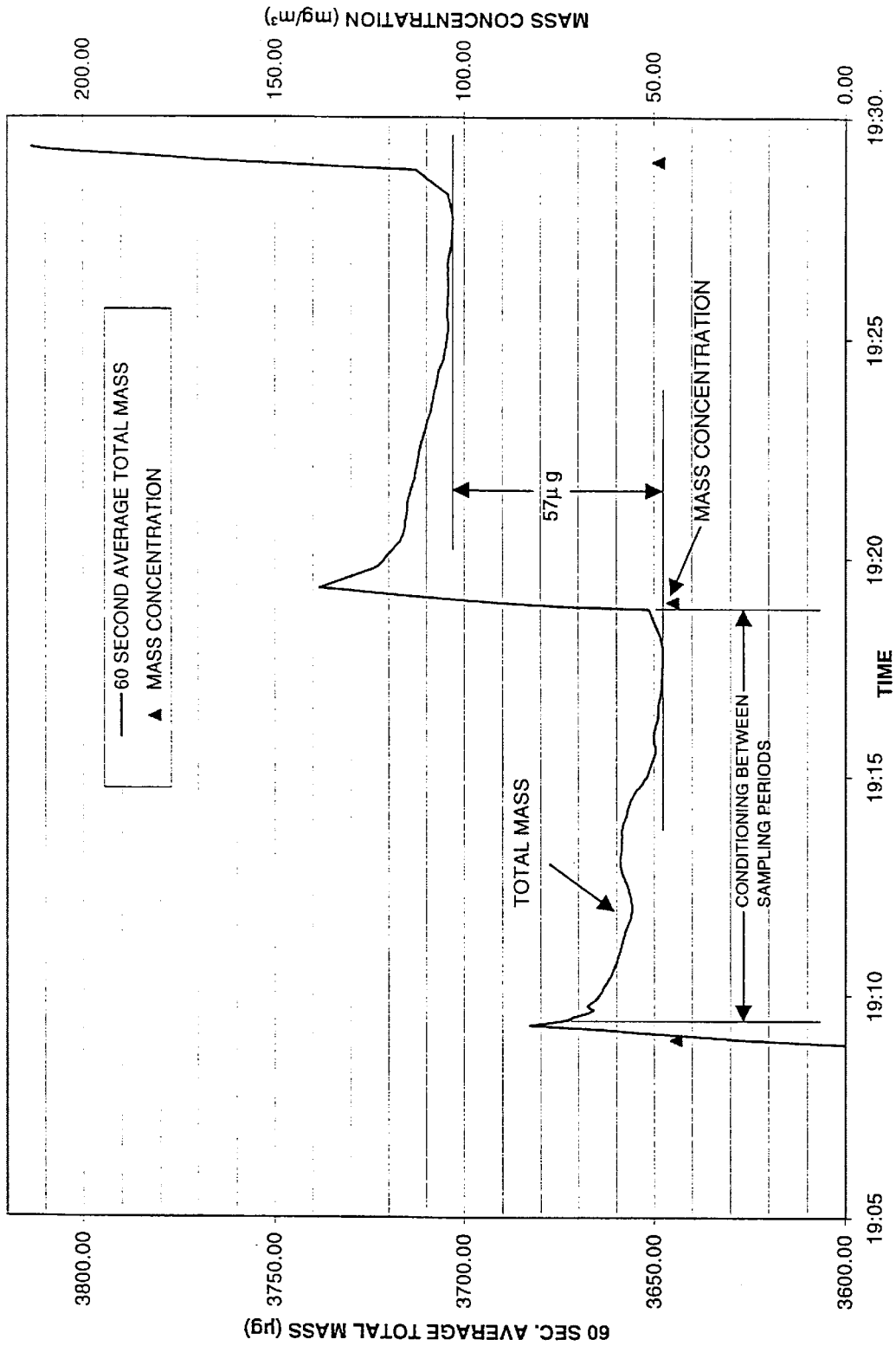
FIG. 4 provides a graphical representation of in-stack conditioning between intermittent sampling periods.

As illustrated in FIG. 4, the conditioned gas may also be advantageously used to condition the collector between time proportioned (i.e. intermittent) sampling periods. The difference in total mass readings between consecutive stabilized conditioning periods provides a measure of the mass increase occurring during the intermediate sampling period.

The present invention is directed to a further refinement of the above-described particulate mass measuring instrument and method. This refinement eliminates or reduces inertial mass measurement errors resulting from changes in pressure across the particulate collector and/or changes in sampling flow rate from the collector, and thereby ensures greater accuracy in weighing particulate.

According to the present invention, a pressure measurement across the particulate collector 40, e.g. a filter, is used to calibrate mass measurement assembly 16, in the stack, and to adjust mass readings provided by instrument 10 in order to compensate for pressure changes across the collector during sampling.

Figure 5:
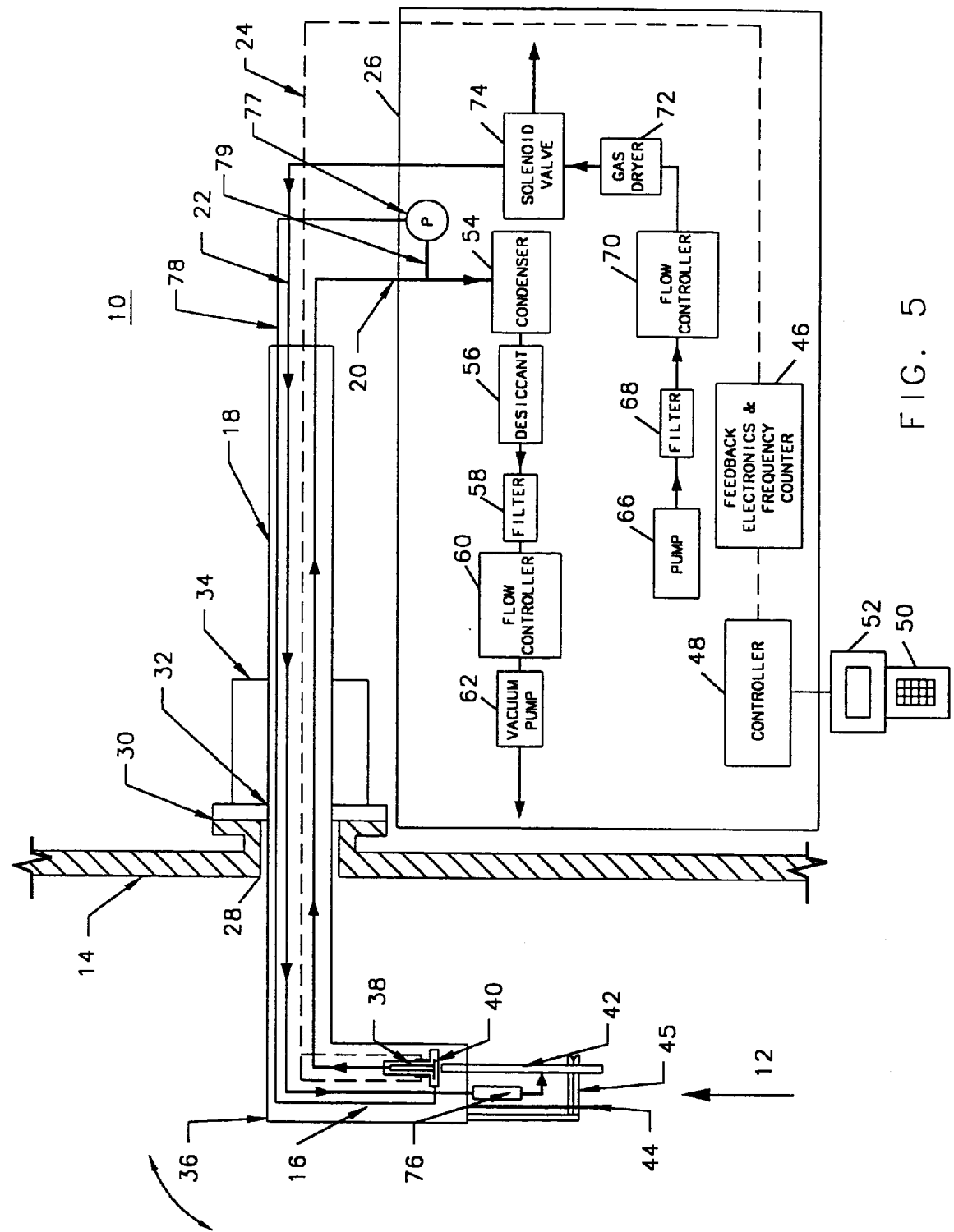
FIG. 5 depicts the particulate mass measurement apparatus of FIG. 1, further adapted to include a pressure/flow compensator.

FIG. 5 depicts the particulate mass measurement instrument 10 of FIG. 1 enhanced with the pressure/flow compensation features of the present invention. For clarity of depiction, the pressure/flow compensation components are shown in isolation in FIG. 6.

Pressure changes across particulate collector 40 of instrument 10 occur when flow controller 60 varies the sampling flow rate along sampling line 20 in order to maintain isokinetic sampling. Inertial mass measurement devices, such as mass transducer 38, exhibit a pressure dependence that may result in erroneous mass readings if such pressure changes are not properly controlled or accounted for.

Figure 6:
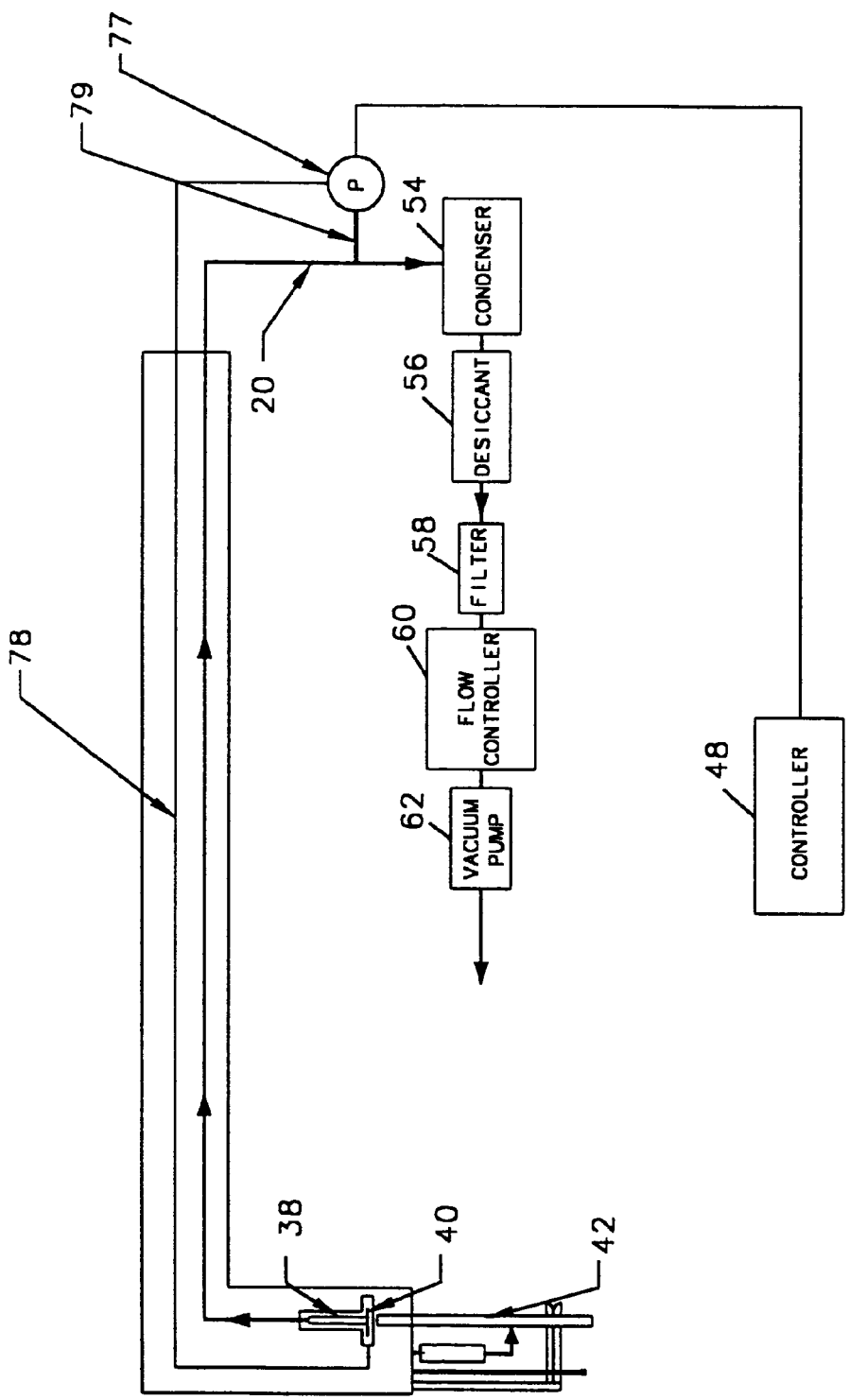
FIG. 6 is a simplified depiction of the pressure/flow compensator of FIG. 5.

According to the present invention, pressure compensation of mass measurement instrument 10 involves measurement of a pressure differential across particulate collector 40. This measurement is preferably accomplished using a differential pressure transducer 77, located in control unit 26, as shown in FIG. 5. To measure the pressure differential across collector 40, a first pressure tap line 78 extends from pressure transducer 77 to a position in assembly 16 upstream of collector 40. A second pressure tap line 79 connects pressure transducer 77 to sampling line 20 to sense a pressure downstream of collector 40. Pressure transducer 77 measures the pressure differential across collector 40 and provides an output reading to controller 48. Communication between transducer 77 and controller 48 is depicted in FIG. 6.

In those instances where there is no pressure drop between the effluent gas 12 in stack 14 and the upstream side of collector 40, first pressure tap line 78 may be eliminated and the existing pressure sensor 45 may be used to provide the first pressure reading. Further, if the static pressure in the stack is at or near ambient pressure, which it typically is, pressure tap line 78 may be eliminated and the corresponding side of pressure transducer 77 may be left open to atmosphere.

A suitable exemplary differential pressure transducer for use in the pressure compensator of the present invention is available from Data Instruments, of Acton, Mass. under Model No. XCA 4150. The other components of pressure compensated mass measuring instrument 10 of FIG. 5 are identical to and operate in the same fashion as their counterparts in FIG. 1. The methodology implemented by the instrument is also the same except for the addition of a pressure calibration operation and pressure compensation of the mass measurements. The supplementary steps will now be described in detail.

Pressure calibration is achieved by comparing the resonant frequency of mass transducer 38 at two different flow/pressure conditions with no mass uptake ($\Delta m'=0$). In this procedure, collector 40, e.g. an exchangeable filter cartridge, is placed on the free end of mass transducer 38. Mass measurement assembly 16 is then placed in stack 14, and collector 40 is preferably equilibrated in-situ by the conditioned gas stream. The conditioned gas stream brings collector 40 to a stabilized state and prevents mass uptake on the collector during the calibration procedure. A constant flow $F_1$ is drawn through mass transducer 38 by pump 62 and flow controller 60. Resonant frequency $f_1$ of transducer 38 is determined by feedback electronics and frequency counter 46 while pressure transducer 77 measures a pressure differential $P_1$ across collector 40 for constant flow $F_1$. Frequency $f_1$ and pressure $P_1$ are provided to controller 48. The flow of sampled gas along sampling line 20 is then controllably varied a small increment by flow controller 60 to a second constant flow rate $F_2$. Frequency $f_2$ and pressure $P_2$ for flow rate $F_2$ are similarly determined and provided to controller 48. Controller 48 then calculates the pressure coefficient of frequency PC using the above determined values in accordance with the following equation. The units of this coefficient are typically: hertz/hertz/pounds per square inch $$PC=(f_2-f_1)/((f_2+f_1)/2)/(P_2-P_1) \quad (10)$$

where:
 $f_1$ and $P_1$ are the measured resonant frequency of mass transducer 38 and the measured pressure differential across collector 40, respectively, at flow rate $F_1$
 $f_2$ and $P_2$ are the measured resonant frequency of mass transducer 38 and the measured pressure differential across collector 40, respectively, at flow rate $F_2$ The above described pressure calibration procedure is advantageously initiated after collector 40 has been equilibrated and preconditioned in-situ and before sampling occurs. The pressure coefficient of frequency PC can be stored by controller 48 for subsequent use in compensating mass readings. Alternatively, a flow coefficient of frequency FC may be calculated using the following equation. The units of the flow coefficient are typically: hertz/hertz/liters per minute $$FC=(f_2-f_1)/((f_2+f_1)/2)/(F_2-F_1) \quad (11)$$

The pressure coefficient of frequency PC or the flow coefficient of frequency FC can be used to refine the mass calculations of instrument 10. The presently preferred pressure compensation approach will now be described with reference to the preferred hollow elastic tube mass transducer.

Once $K_0$ is determined for a particular elastic element, as hereinabove described, and a pressure coefficient of frequency PC has been determined for the collector mounted on the element, these values can be used to determine adjusted or corrected mass readings. If the elastic element is oscillating at a frequency $f_a$ and subsequently exhibits a frequency of $f_b$ after an unknown mass uptake $\Delta m'$ and a measured pressure drop change $\Delta P$, this mass update can be obtained using the following equations.

$$fa = \sqrt{K_0/m} \quad (12)$$

$$f_{bc} = \sqrt{K_0/(m+\Delta m')} + (PC*(\Delta P)*((f_b+f_a)/2) \quad (13)$$

Where:
m=total mass of the oscillating system
$\Delta P$=the change in pressure across the collector
$f_{bc}$=pressure compensated frequency reading
Pressure compensated mass uptake $\Delta m'_c$ is calculated as follows.

$$\Delta m'_c = K_0(1/f_{bc}^2 - 1/f_a^2) \quad (14)$$

In practice, pressure transducer 77 determines the change in pressure across the collector $\Delta P$ while frequencies $f_a$ and $f_b$ are provided by feedback electronics and frequency counter 46. The calculations of the pressure compensated frequency reading $f_{bc}$ and the pressure compensated mass uptake $\Delta m'_c$ are done by controller 48. Consecutive $\Delta m'_c$ can be summed to define and depict the total mass TM added to the collector, as illustrated in FIG. 7. For comparison purposes, FIG. 7 illustrates the total mass TM with and without the pressure compensation of the present invention along with the corresponding measured pressure differential. As depicted, the pressure compensator of the present invention provides a more accurate measure of the mass of the collected particulate matter.

In a similar manner, once $K_0$ and a flow coefficient of frequency FC have been determined as earlier described, flow compensated mass uptake can be obtained using the following equation.

$$fa = \sqrt{K_0/m} \quad (15)$$

$$f_{bc} = \sqrt{(K_0/(m+\Delta m'))} + (FC*(\Delta F)*((f_b+f_a)/2) \quad (16)$$

Where:
m=total mass of the oscillating system
$\Delta F$=the measured change in flow through the mass transducer The fundamental equation for flow compensated mass uptake is as follows.

$$\Delta m'_c = K_0(2/f_{bc}^2 - 1/f_a^2) \tag{17}$$

The flow rate change ΔF can be readily measured using the flow sensor portion of flow controller 60. Again, the frequency readings are provided by feedback electronics and frequency counter 46; controller 48 calculates the flow compensated mass uptake.

The present invention retains all of the advantages of the mass measuring instrument 10 of FIG. 1 while providing for further refined pressure or flow compensated mass reading. When integrated with the other features and aspects of particulate mass measuring instrument 10, the pressure/flow compensator of the present invention provides enhanced benefits.

From the above description, it will be readily apparent to those skilled in this art that an in-stack particulate mass measurement instrument has been provided which overcomes many of the disadvantages of the prior art and provides additional benefits. The need for pre- and post-conditioning and weighing of a particulate collector in a laboratory is eliminated as are the many opportunities for errors associated with this prior technique. The conditioned gas line of the measurement instrument allows for quick, easy in-stack equilibration both before and after sampling. The use of an inertial mass measurement transducer permits direct on-line near real-time mass measurement of collected particulate. The mass readings are directly available at the site, eliminating the need to transport the sample to a lab for postconditioning and weighing. Since it resolves mass in near real-time, the present instrument provides useful plant process information such as transient particulate mass concentrations during ramped loadings, stratification in stacks and control device efficiencies. It also facilitates the calibration of existing indirect continuous emission monitors. Any particulate matter collected on the inlet tube wall during sampling can be subsequently loosened, collected and immediately weighed by the same instrument, resulting in an EPA Method 17 equivalent test. The pressure/flow compensator of the present invention reduces or eliminates measurement errors attributable to pressure/flow changes and therefore, enhances the accuracy of the instrument. Operation of the instrument of the present invention reduces testing errors and provides an accurate and repeatable test protocol. The pressure/flow compensator and other teachings of the present invention can also advantageously be employed in mass measurement devices used in applications beyond stack monitoring, e.g. where sampling flow rates are varied for other reasons or where pressure changes across the collector attributable to other causes, or simply to mass loading, require compensation.

Although presently preferred embodiments of the invention have been described and depicted herein, those skilled in the art will recognize that various modifications, substitutions and additions can be made without departing from the principles of this invention.

What is claimed is:

1. Apparatus for directly measuring mass of particulate of effluent gas flowing in a stack, comprising:

an inertial mass measurement assembly including a mass transducer, a particulate collector connected to said mass transducer, and an inlet tube for directing sampled gas toward said collector;

a support structure for supporting said mass measurement assembly within said stack with said inlet tube oriented for sampling effluent gas flowing in said stack whereby sampled effluent gas enters said tube and is directed toward said collector, and particulate in said sampled effluent gas is collected by said collector;

a pressure transducer for measuring a pressure differential across said collector; and a processor for determining an adjusted mass reading of said collected particulate based upon an output from said mass transducer and said measured pressure differential.

2. The apparatus of claim 1 wherein said pressure transducer measures a differential between a first pressure upstream of said collector and a second pressure downstream of said collector.

3. The apparatus of claim 2 wherein said first pressure comprises ambient air pressure.

4. The apparatus of claim 2 wherein said first pressure comprises a pressure of said effluent gas flowing in said stack.

5. The apparatus of claim 2 further including a first pressure tap line for sensing said first pressure, and a second pressure tap line for sensing said second pressure, said first pressure tap line and said second pressure tap line being connected to said pressure transducer.

6. The apparatus of claim 1 further including a sampling line for conveying sampled gas from said collector to a control unit outside said stack, said control unit including a flow controller for varying flow of said sampled gas in said sampling line to maintain isokinetic sampling of the effluent gas at an entrance to said inlet tube; and wherein said pressure transducer measures a pressure differential across said collector related to said varying sampled gas flow.

7. The apparatus of claim 1 wherein said mass transducer comprises a hollow elastic element mounted to vibrate in a clamp-free mode, the collector comprises a filter mounted on a free end of said elastic element, and the sampled gas is drawn through said filter and said hollow elastic element.

8. The apparatus of claim 1 further comprising an in-situ equilibrator for equilibrating the collector within said stack.

9. The apparatus of claim 8 wherein said in-situ equilibrator comprises a supply line for selectively supplying conditioned gas to said collector while said mass measurement assembly is supported within said stack, and wherein said conditioned gas prevents effluent gas from reaching said collector; and further comprising:

a controller mandating supply of said conditioned gas to said collector prior to a sampling period to precondition said collector, and calibration means for determining a pressure coefficient of frequency of said mass transducer with connected collector following collector preconditioning.

10. The apparatus of claim 9 wherein said calibration means includes said pressure transducer, and wherein said pressure coefficient of frequency is used by said processor for determining said adjusted mass reading.

11. The apparatus of claim 10 wherein said pressure coefficient of frequency is determined in accordance with the following formula:

$$PC = (f_2 - f_1)/((f_2 + f_1)/2)/(P_2 - P_1)$$

where:

PC represents the pressure coefficient of frequency;

$f_1$ and $P_1$ represent a frequency of oscillation of the mass transducer, and a pressure differential measured by said pressure transducer, respectively, at a time $T_1$; and $f_2$ and $P_2$ represent a frequency of oscillation of the mass transducer, and a pressure differential measured by said pressure transducer, respectively, at a time $T_2$.

12. The apparatus of claim 11 wherein said time $T_1$ is associated with a first sampled gas flow rate from said collector, and the time $T_2$ is associated with a second different sampled gas flow rate from the collector.

13. The apparatus of claim 1, wherein said mass transducer has a mechanical resonant frequency, and further comprising calibration means for determining a pressure coefficient of frequency of said transducer with connected collector.

14. The apparatus of claim 13, wherein said calibration means includes said pressure transducer, and wherein said pressure coefficient of frequency is used by said processor for determining said adjusted mass reading.

15. A mass measurement device wherein material from a flow of a sampled gas is collected on a collector for mass measurement purposes and an inertial mass transducer associated with said collector provides an output representative of a reading of mass of the collected material, further comprising:

a pressure transducer for measuring a pressure differential for the gas flow across said collector for a gas sampling period; and a processor for determining an adjusted mass reading of collected material based upon said output and said measured pressure differential for the gas sampling period.

16. The mass measurement device of claim 15 wherein said collector comprises a filter mounted on a free end of a hollow elastic element having a natural frequency of vibration the flow of sampled gas is drawn through said filter and hollow elastic element, and said pressure transducer measures a differential between a first pressure upstream of said filter and a second pressure downstream of said filter.

17. The mass measurement device of claim 16 wherein said first pressure comprises ambient air pressure.

18. The mass measurement device of claim 16 wherein said processor determines said adjusted mass reading based upon said output, said measured pressure differential and a pressure coefficient of frequency for said elastic element with mounted filter.

19. The mass measurement device of claim 15, wherein said mass transducer has a mechanical resonant frequency, and further comprising calibration means for determining a pressure coefficient of frequency of said transducer with associated collector.

20. The mass measurement device of claim 19, wherein said calibration means includes said pressure transducer, and wherein said pressure coefficient of frequency is used by said processor for determining said adjusted mass reading.

21. A method for measuring mass of material in an effluent gas flowing in a stack, comprising:

locating an inertial mass measurement assembly within said stack, said assembly including a material collector mounted to an inertial mass measurement transducer having a mechanical resonant frequency;

calibrating the transducer with mounted collector to generate a pressure coefficient of frequency therefor;

collecting material from sampled effluent gas on the collector within the stack during a sampling period; and measuring a mass change of said collector for the sampling period with said inertial mass measurement assembly and providing an output from said assembly representative of said mass change for the gas sampling period.

22. The method of claim 21 further comprising:

measuring change in pressure across said collector for said sampling period; and employing said output, said pressure coefficient of frequency and measured change in pressure to derive an adjusted mass reading of collected material for said sampling period, wherein said adjusted mass reading accounts for effects attributable to said change in pressure.

23. In a method of measuring mass of particulate collected from a gas stream by a collector mounted to a mass transducer of an inertial mass measurement assembly, wherein the assembly provides an output representative of a reading of mass of the collected particulate, the improvement comprising:

compensating said reading in response to a measured change in pressure for the gas stream across said collector for the gas sampling period.

24. The improved method of claim 23 wherein said mass transducer has a natural frequency of oscillation, and said compensating comprises:

determining a pressure coefficient of frequency for said mass transducer with mounted collector;

measuring a change in pressure across said collector for a sampling period; and employing said output, said pressure coefficient of frequency and measured change in pressure to derive an adjusted mass reading of the collected particulate for said sampling period, wherein said adjusted mass reading accounts for effects attributable to said change in pressure across the collector.

25. A mass measurement device wherein material from a flow of a sampled gas is collected on a collector for mass measurement purposes and an inertial mass transducer associated with said collector provides an output representative of a reading of mass of said collected material collected for a gas sampling period, further comprising:

a flow sensor for measuring change in flow rate of sampled gas exiting said collector for a gas sampling period; and a processor for determining an adjusted mass reading of said collected material based upon said output and said measured change in flow rate for the gas sampling period.

\* \* \* \* \*

UNITED STATES PATENT AND TRADEMARK OFFICE
CERTIFICATE OF CORRECTION

PATENT NO. : 6,016,688
DATED : January 25, 2000
INVENTOR(S) : Hiss, III et al.

It is certified that error appears in the above-identified patent and that said Letters Patent is hereby corrected as shown below:

Claim 23, Col. 16, line 25, after "particulate" insert --for a gas sampling period--.

Signed and Sealed this

Third Day of October, 2000

Attest:

Q. TODD DICKINSON

*Attesting Officer*  *Director of Patents and Trademarks*